United States Statutory Invention Registration [19]

[11] Reg. Number: H675

Wortman et al.

[43] Published: Sep. 5, 1989

[54] METHOD FOR CHEMICAL REACTION CONTROL USING A SURFACE ACOUSTIC WAVE DEVICE

[75] Inventors: Donald E. Wortman, Rockville; Clyde A. Morrison, Wheaton; Frank J. Crowne, Laurel; Richard Leavitt, Berwyn Heights, all of Md.

[73] Assignee: The United States of America as represented by the Secretary of the Army, Washington, D.C.

[21] Appl. No.: 928,714

[22] Filed: Nov. 4, 1986

Related U.S. Application Data

[62] Division of Ser. No. 676,463, Nov. 29, 1984, abandoned.

[51] Int. Cl.[4] ..... C12P 7/34

[52] U.S. Cl. ..... 436/152; 422/194; 422/98; 436/159; 73/DIG. 4

[58] Field of Search ..... 422/177, 180, 186, 127, 422/128, 94, 96, 98; 423/213.2, 213.5; 310/313 R, 313 A; 436/152, 159; 73/DIG. 4

[56] References Cited

U.S. PATENT DOCUMENTS

| | | | |
|---|---|---|---|
| 2,745,861 | 5/1956 | Bodine, Jr. | 260/449 |
| 3,194,640 | 7/1965 | Nesh | 23/283 |
| 3,637,354 | 1/1972 | Smithson et al. | 423/213.5 |
| 3,827,002 | 7/1974 | Chao | 310/313 A |
| 3,945,804 | 3/1976 | Shang et al. | 23/288 E |
| 4,055,072 | 10/1977 | Fletcher et al. | 73/23 |
| 4,055,758 | 10/1977 | Stern et al. | 310/313 R |
| 4,142,163 | 2/1979 | Phillips | 333/194 |
| 4,233,573 | 11/1980 | Grudkowski | 310/313 R |
| 4,243,960 | 1/1981 | White et al. | 333/196 |
| 4,259,726 | 3/1981 | Joly | 310/313 R |
| 4,312,228 | 1/1982 | Wohltjen | 310/313 R |
| 4,343,688 | 8/1982 | Harwood | 310/313 R |
| 4,361,026 | 11/1982 | Muller et al. | 73/23 |
| 4,495,431 | 1/1985 | Grudkowski | 333/154 |
| 4,544,857 | 10/1985 | Shimiyu et al. | 310/313 A |
| 4,572,900 | 2/1986 | Wohltjen | 422/94 |
| 4,586,077 | 4/1986 | Wonn et al. | 333/193 |
| 4,598,224 | 7/1986 | Ballato | 422/98 |

OTHER PUBLICATIONS

Julius Grant, ed., *Hackh's Chemical Dictionary,* 4th edition, McGraw-Hill Book Co. (New York), 1972, p. 529.

Caserta et al., Proc. Nat. Acad. Sci. U.S.A., vol. 71, No. 11, pp. 4421-4424, Nov. 1974.

D'Amico et al., *Appl. Phys. Lett.,* 41(3), 8/1/82, pp. 300-301.

James E. Brady; Fundamentals of Chemistry; Copyright 1981 by John Wiley & Sons, pp. 475-478, 767, and 771.

Traugott E. Fischer; "A New Look at Catalysis", Physics Today, May 1974, pp. 23-28.

Tsong et al., "Field Induced and Surface Catalyzed Formation of Novel Ions: A Pulsed-Laser Time-of-Flight Atom-Probe Study", J. Chem. Phys. 78(7), Apr. 1, 1983, pp. 4763-4775.

Weast et al., *Handbook of Chemistry and Physics,* Library of Congress Card No. 13-11056, p. F-34, definition of "Catalytic Agent".

Slobodnik, Jr., "Surface Acoustic Waves and SAW Materials", Proc. I.E.E.E., vol. 64, No. 5, p. 581, May 1976.

McGraw-Hill Dictionary of Physics and Mathematics, Copyright 1978, pp. 579, 816 and 957.

Report HDL-TR-1752, A Possible Use of the Surface States of Transition and Rare-Earth Metal Ions in the Theory of Catalysis, by Morrison, Karayianis and Wortman, Apr. 1976, Harry Diamond Laboratories, Adelphi, Md. 20783.

Phenomenological Theory of the Acoustophotorefractive Effect, by Richard P. Leavitt, Appl. Phys. Lett. 34 (11), Jun. 1, 1979, pp. 771-773.

"Ultrasound is Used to Initiate Catalytic Reactions", p. 70, Industrial Research & Development, Jun. 1982.

"Quantum Chemistry and Catalysis", by Slater and Johnson, pp. 34-41, Physics Today, Oct. 1974.

*Primary Examiner*—John F. Terapane
*Assistant Examiner*—Daniel S. Metzmaier
*Attorney, Agent, or Firm*—Saul Elbaum; Thomas E. McDonald

[57] ABSTRACT

A method and apparatus for controlling a chemical reaction by heterogeneous catalysis, in which a surface acoustic wave (SAW) is propagated along a surface of a piezoelectric element in contact with liquid or gaseous substances to be chemically reacted, to thus generate an electric field at the surface of the element which initiates and sustains the desired reaction. The catalysis rate can be varied by varying the frequency and/or intensity of the surface acoustic wave. The surface of the element may be coated with a very thin film of a catalytic group 8 metal which can be penetrated by the SAW electric field. In such an embodiment, normal catalysis proceeds via chemisorption, and the SAW element field acts to increase the catalysis rate.

10 Claims, 2 Drawing Sheets

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR CHEMICAL REACTION CONTROL USING A SURFACE ACOUSTIC WAVE DEVICE

RIGHTS OF THE GOVERNMENT

The invention described herein may be manufactured, used, and licensed by or for the United States Government for governmental purposes without payments to us for any royalty thereon.

This application is a division of application Ser. No. 676,463, filed Nov. 29, 1984, now abandoned.

BACKGROUND OF THE INVENTION

The invention relates generally to the control of chemical reactions by heterogeneous catalysis, and, more particularly, to the control of the catalytic reaction by a surface acoustic wave (SAW) device.

Most catalysts of current use in heterogeneous catalysis contain one or more transition metals which provide active electronic surfaces which stimulate the catalytic action. For single crystals of a transition element, such as platinum, the catalytic reaction is more efficient if the crystal is cleaved along certain crystallographic planes. This indicates that the surface states are a function of the crystallographic plane. These surface states determine the electric field near the metal surface. This electric field controls certain catalytic reactions that take place near the surface.

Most of the transition metals used as catalysts are group 8 elements. In particular, platinum and platinum-type metals, which are relatively rare and costly elements which must be imported from countries such as the U.S.S.R. and South Africa, are widely used in catalytic conversion devices such as fuel cells and in many energy conversions schemes used by the petroleum industry and in chemical processes in general. It would be highly desirable if the quantity of platinum and platinum-like metals required in such catalytic conversion devices could be reduced, or if abundant, inexpensive, group 8 elements such as iron, cobalt, or nickel, could be used in these catalytic conversion devices in Place of platinum or platinum-like elements. Further, it would be highly desirable to eliminate the need of any transition elements in certain heterogeneous catalysis processes.

It is known that the propagation of an acoustic wave along the surface of a piezoelectric material creates an electric field adjacent this surface, and that the intensity and shape of this electric field can be controlled by appropriate doping of the piezoelectric material and by the frequency and intensity of the surface acoustic wave (SAW). Also, it is known to adjust the center frequency of a SAW device by depositing a film of electrically nonconducting material on the surface of the piezoelectric material along which the SAW is propagated, as described in White et al. U.S. Pat. No. 4,243,960, issued Jan. 6, 1981.

SUMMARY OF THE INVENTION

It is an object of the invention to provide a method of controlling a chemical reaction by heterogeneous catalysis, which does not require a catalyst containing a transition element.

It is another object of the invention to provide a method for controlling a chemical reaction by heterogeneous catalysis, which minimizes the quantity of transition elements required in the catalyst.

It is still another object of the invention to provide a method for controlling chemical reaction by heterogeneous catalysis, in which the catalyst comprises a relatively inexpensive, easily attainable transition element.

It is yet another object of the invention to provide a SAW device for controlling a chemical reaction by heterogeneous catalysis.

It is a further object of the invention to provide a SAW catalytic converter, in which a thin film of catalytic material including a transition element, is disposed on a piezoelectric substrate in contact with the substances to be catalytically converted, wherein the electric field generated at the surface of the piezoelectric element by a surface acoustic wave propagated therealong augments the electric field of the transition element.

In the method and apparatus according to the invention, a surface acoustic wave (SAW) is propagated along a surface of a piezoelectric element so as to generate a strong electric field at this surface, and liquid or gaseous substances to be chemically reacted are directed to this surface. The electric field created by the SAW at this surface acts in the same manner as an electric field of a transition element, such as platinum, to initiate and control the catalytic reaction of the substances.

Also, the surface of the piezoelectric element can be coated with a film of catalytic material containing a transition metal, which is so thin that the SAW electric field penetrates the film and augments the electric field of the transition element. The surface acoustic wave can then be varied in frequency and intensity to control the catalytic process. By using this SAW device in a catalytic conversion process which normally utilizes a platinum or platinum-like catalyst, the quantity of platinum required for a given reaction is minimized. Also, since the SAW electric field augments the electric field of the catalytic material, a less expensive, easily attainable group 8 transition element such as iron, cobalt or nickel, can be used instead of platinum or a platinum-like element to achieve the same catalytic reaction.

BRIEF DESCRIPTION OF THE DRAWINGS

The invention will be better understood, and further objects, features, and advantages thereof will become more apparent from the following description of preferred embodiments, taken in conjunction with the accompanying drawings in which.

DESCRIPTION OF PREFERRED EMBODIMENTS

Figure 1:
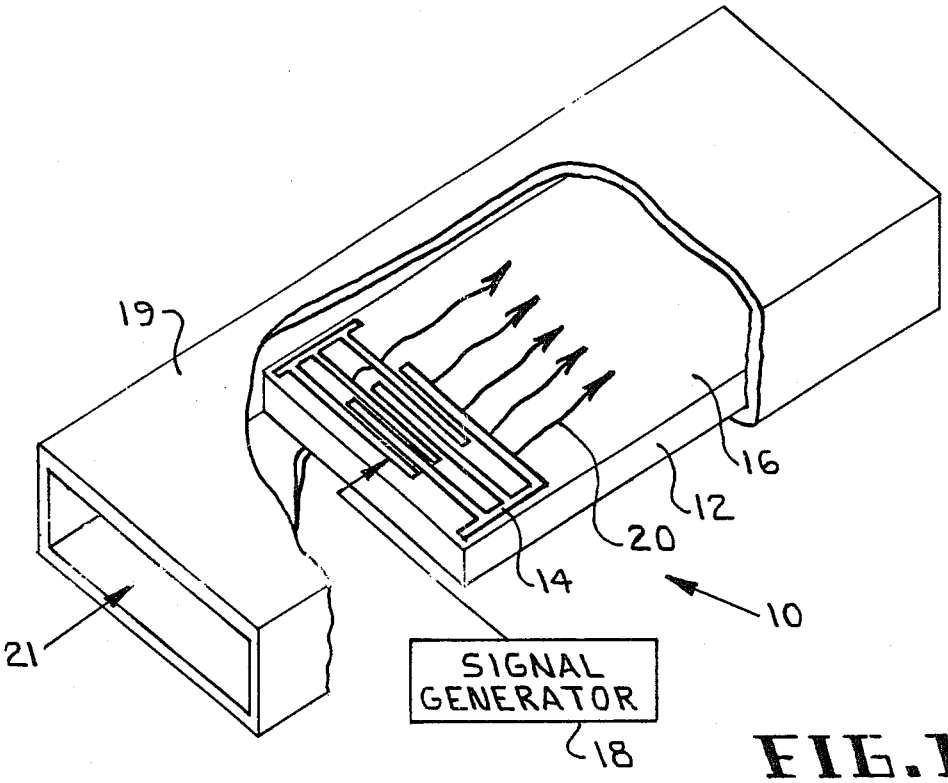
FIG. 1 is a perspective view of the SAW device in a first embodiment of the invention with an exterior portion removed to show interior portions.

The SAW device 10 shown in FIG. 1 includes a sheet 12 of piezoelectric crystal, such as $Bi_{12}Ge\,O_{20}$, $Bi_4Ge_3O_{12}$, or lithium niobate, $LiNbO_3$. At least one acoustic transducer 14 is disposed on the surface 16 of the piezoelectric crystal 12. The acoustic transducer 14 converts an alternating electrical signal generated by a signal generator 18 to a corresponding acoustic wave 20 which is propagated along the surface 16 of the piezoelectric crystal 12. Typically, each transducer 14 consists of two sets of interdigital metallic fingers, with each set connected to a common connector.

The surface acoustic wave 20 produces a corresponding electric field at the surface 16 along which the acoustic wave 20 is propagated.

The piezoelectric crystal 12 is disposed in a vessel or passageway 19 through which liquid or gaseous substances 21 to be catalytically converted are directed to the surface 16 of the piezoelectric crystal 12. The electric field generated by the SAW 20 acts in the same manner as the electric field of a transition element, such as platinum, to initiate and sustain the desired chemical reaction of these substances.

Figure 2:
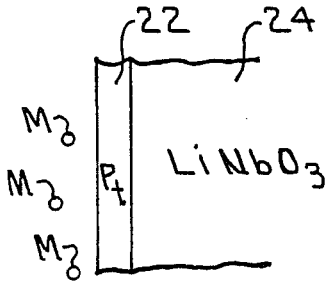
FIG. 2 is a diagrammatic representation of the SAW device in a second embodiment of the invention.
Figure 3:
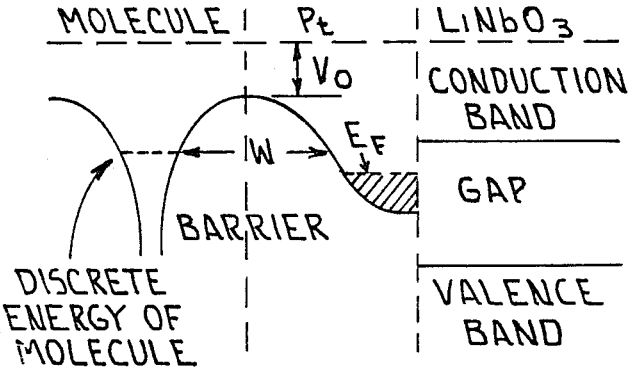
FIG. 3 is an energy diagram illustrating the electron tunneling effect created by the electric field of the catalyst in the embodiment of FIG. 2.

For certain chemical processes where chemisorption is desirable, a film of catalyst material including a transition element can be deposited on the surface 16 of the piezoelectric crystal 12. This deposited film must be very thin, less than a micron in thickness, to allow the electric field generated by the surface acoustic wave 20 to penetrate this film. For example, when a thin film 22 of platinum is deposited on a lithium niobate substrate 24 as shown diagrammatically in FIG. 2, molecules M of substances to be chemically reacted are catalyzed by the platinum. Normal catalysis proceeds via chemisorption; a molecule M gets close enough to the platinum film 22 to contribute an electron via tunnelling; this electron finds its way to a neighboring molecule and the two molecules react together. The energy barrier to tunnelling, shown in FIG. 3, determines the rate at which the catalysis proceeds.

Figure 4:
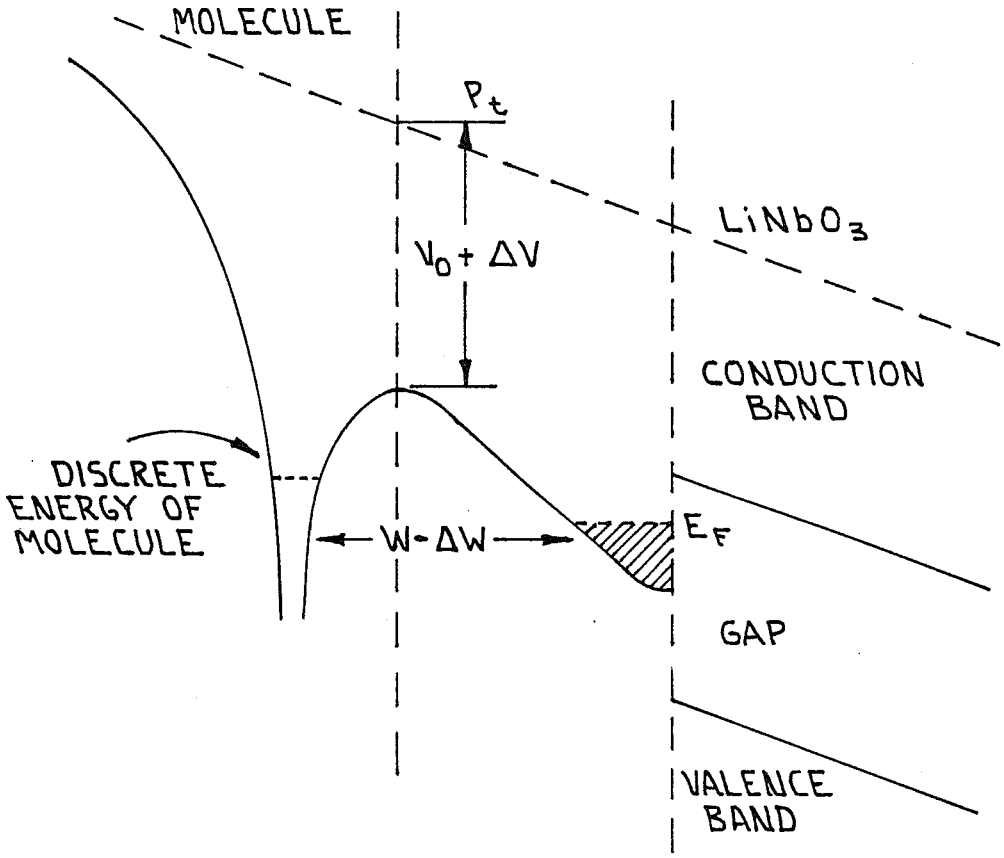
FIG. 4 is an energy diagram illustrating the electron tunneling effect created by the catalyst electric field augmented by the SAW electric field in the embodiment of FIG. 2.

If now, a SAW electric field penetrates the platinum film, this SAW electric field will augment the fixed electric field of the platinum film and affect the energy barrier to tunnelling, as shown by in FIG. 4. Note that the SAW field, which puts the energy diagram on a "slant", lowers the barrier by an amount $\Delta V$ and "thins" it by an amount $\Delta W$. Since the tunnelling action is very sensitive to the energy barrier, the SAW electric field can greatly increase the catalysis rate. The catalysis rate can be varied by varying the SAW intensity or frequency.

Also, since the SAW electric field does augment the normal catalytic action of the platinum film, this platinum film can be replaced by a film of another transition element, such as iron or nickel, since the Fermi level $\epsilon_F$ can be made to shift as can the potential barrier width.

Since there are many variations, modifications, and additions to the specific embodiments of the invention described herein which would be obvious to one skilled in the art, it is intended that the scope of the invention be limited only by the appended claims.

What is claimed and desired to be secured by Letters Patent of the United States is:

1. A method of controlling a chemical reaction of liquid or gaseous substances by heterogeneous catalysis, comprising the steps of:

directing the substances to be chemically reacted to a surface of a piezoelectric element; and propagating a surface acoustic wave (SAW) along said element surface to generate an electric field which initiates and controls the catalytic reaction of said substances at said element surface.

2. A method, as described in claim 1, wherein said element surface comprises a thin film of a metallic catalyst which includes at least one transition element, said film being so thin that the SAW electric field penetrates the film.

3. A method, as described in claim 1, which further comprises the step of adjusting at least one characteristic of said acoustic wave to adjust said electric field generated by said acoustic wave, thereby adjusting the rate of catalysis of said substances which is controlled by said electric field.

4. A method, as described in claim 2, wherein said metallic catalyst film is less than one micron thick.

5. A method, as described in claim 2, where said metallic catalyst film includes a group 8 transition element.

6. A method, as described in claim 4, wherein said group 8 transition element is platinum.

7. A method, as described in claim 4, wherein said group 8 transition element is iron.

8. A method, as described in claim 4, wherein said group 8 transition element is cobalt.

9. A method, as described in claim 4, wherein said group 8 transition element is nickel.

10. A method, as described in claim 1, wherein:

at least one acoustic transducer is disposed on said element surface, said at least one acoustic transducer comprising two sets of interdigital metallic fingers, with each set connected to a common connector; and the step of propagating a surface acoustic wave along said element surface comprises the step of applying an alternating electrical signal across the two sets of said at least one acoustic transducer.

* * * * *